(12) United States Patent
Lawyer et al.

(10) Patent No.: US 7,576,133 B2
(45) Date of Patent: Aug. 18, 2009

(54) METHODS AND COMPOSITIONS FOR NASAL ADMINISTRATION OF MODAFINIL

(76) Inventors: Carl Henry Lawyer, 1918 Jeanette La., Unit #7, Springfield, IL (US) 62702; Matthew Carl Lawyer, 1918 Jeanette La., Unit #7, Springfield, IL (US) 62702; Edward Zadok Lawyer, 1918 Jeanette La., Unit #7, Springfield, IL (US) 62702

( * ) Notice: Subject to any disclaimer, the term of this patent is extended or adjusted under 35 U.S.C. 154(b) by 0 days.

(21) Appl. No.: 10/384,044

(22) Filed: Mar. 7, 2003

(65) Prior Publication Data

US 2003/0171439 A1    Sep. 11, 2003

Related U.S. Application Data

(60) Provisional application No. 60/362,931, filed on Mar. 11, 2002.

(51) Int. Cl.
*A61K 31/165* (2006.01)
(52) U.S. Cl. .................................... 514/619
(58) Field of Classification Search ................ 514/618, 514/619
See application file for complete search history.

(56) References Cited

U.S. PATENT DOCUMENTS 5,618,845 A    4/1997    Grebow et al. .............. 514/618

FOREIGN PATENT DOCUMENTS

GB    2293103    *    3/1996

OTHER PUBLICATIONS

Remington's Pharmaceutical Sciences, 18th ed., 1990, pp. 1132-1134, 1613, 1629-1632, and 1694-1712.*
Remington's Pharmaceutical Sciences, 18th ed., 1990, pp. 1316-1317.*
Abstract of Jasinski et al., Clinical Neuropharmacology, 2000;23(3):149-156.*
Hou et al., Zhongguo Yao Li Xue Bao. Sep. 1999;20(9):813-8.*
Section on PROVIGIL, *Physician's Desk Reference*, 2001, p. 1093.

* cited by examiner

*Primary Examiner*—San-ming Hui
(74) *Attorney, Agent, or Firm*—McDonnell Boehnen Hulbert & Berghoff LLP

(57) ABSTRACT

Systemic delivery of Modafinil to the nasal mucous membrane elicits rapid systemic therapeutic response with reduced side effects compared to current methods of administration.

19 Claims, No Drawings

METHODS AND COMPOSITIONS FOR NASAL ADMINISTRATION OF MODAFINIL

CROSS-REFERENCE TO RELATED APPLICATION

This Application claims benefit of priority from U.S. Provisional Application Ser. No. 60/362,931, filed Mar. 11, 2002.

BACKGROUND OF THE INVENTION

1. Field of the Invention

The present invention relates generally to a novel method of administering Modafinil, and to novel dosage forms containing Modafinil adapted for nasal administration.

2. Description of the Prior Art

Modafinil is a racemic compound of chemical formula 2-[(diphenylmethyl)sulfinyl] acetamide. Modafinil is a stimulant, the therapeutic activity of which has been well documented as a wakefulness-promoting agent. Modafinil has been utilized for the treatment of narcolepsy by promoting wakefulness in individuals with excessive daytime sleepiness associated with narcolepsy, and in the treatment of idiopathic hypersomnolence.

Modafinil and its enantiomers are white or whitish crystals that are practically insoluble in water and are only slightly soluble in lower alcohols. The racemic compound has a melting point of 163-165° C. The racemic compound and its enantiomers have the same characteristics stated above. Modafinil currently is administered in oral formulation as a tablet or multiple tablets, or parenterally. However, oral delivery of a therapeutically active amount of Modafinil suffers from a number of disadvantages:

(1) Modafinil administered in an oral formulation is absorbed from the intestinal track at an undesirably slow and uneven rate that leads to undesirable variations in blood levels and undesirably high dosage rates to achieve a therapeutic response leading to undesirable side effects;

(2) Modafinil administered in an oral formulation does not produce desirably high blood levels in a desirably short period of time;

(3) Modafinil administered in an oral formation may result in a significant amount not being absorbed because it is being wasted by metabolism or excretion;

(4) Modafinil administered in an oral formation may lead to further delay of absorption if taken in conjunction with food or other physiologically active agents that slow down the rate of absorption within the gastrointestinal system;

(5) Modafinil administered in an oral formation is administered as a tablet or multiple tablets which may lack the desirable ease of administration because some people may dislike the swallowing of tablets, or may have difficulty swallowing tablets, or are unable to swallow tablets, or may require a liquid to assist swallowing of tablets; and (6) Modafinil-containing tablets also contain several inactive ingredients, including lactose, corn starch, magnesium silicate, croscarmellose sodium, povidone, magnesium stearate, and talc which may be considered undesirable because some people may dislike or be allergic to one or more of these inactive ingredients that comprise the Modafinil tablets.

Thus, there appears a need for improved delivery of Modafinil, which will provide enhanced bioavailability, minimized variations in blood levels, and achieve more rapid onset of activity, as compared to oral dosage forms, while at the same time providing relative ease of administration and reduced side effects compared to current oral delivery methods for administering Modafinil.

SUMMARY OF THE INVENTION

The foregoing and other objects of the invention are achieved by providing methods and compositions for nasal delivery of Modafinil to a mammalian host, particularly a human patient, whereby to provide for rapid absorption of Modafinil to blood circulation while avoiding the above and other disadvantages of oral administration.

More particularly, it has been discovered that Modafinil-containing compositions can be usefully administered to mammals in novel nasal compositions at lower dosage levels to elicit a systemic therapeutic response and provide enhanced bioavailability, minimize variations in blood levels, and achieve more rapid onset of activity, ease of administration, and reduced side effects as compared to conventional oral methods of administration.

DETAILED DESCRIPTION OF PREFERRED EMBODIMENTS

As used herein, the term "Modafinil" is intended to encompass not only Modafinil as the anhydrous powder, but any salt or derivative of Modafinil having wakefulness-promoting activity like Modafinil, and which is non-toxic and pharmacologically acceptable, for example, adrafinil.

"An effective amount," as used herein, is an amount of the pharmaceutical composition that is effective for treating a somnolent or somnolescent state, i.e., an amount of Modafinil of a defined particle size suitable for absorption in the nasal passageway, that is able to reduce or eliminate the symptoms of a somnolescent state or to enhance awareness or to increase regularity of sleep rhythms. An effective amount of a pharmaceutical composition of the invention is useful for reducing or eliminating the symptoms of a somnolescent state or enhancing alertness, or increasing regularity of sleep rhythms.

"A pharmaceutical composition," as used herein, means a medicament for use in treating a mammal that comprises Modafinil of a defined particle size prepared in a manner that is suitable for nasal administration to a mammal. A pharmaceutical composition according to the invention may also, but does not of necessity, include a non-toxic pharmaceutically acceptable carrier.

"A defined particle size," as used herein, means particles having a size sufficiently small so as to be absorbed through the nasal mucous membranes, i.e., smaller than about 100 microns. Preferably, the Modafinil will have a particle size, measured as a dry powder of 1 to 10 microns.

This invention is concerned with the method of nasal administration of Modafinil in compositions containing Modafinil as the sole therapeutic agent or as one of two or more physiologically active agents for delivery to the nasal passage of a mammalian subject.

The current edition of the *Merck Index* may be referenced for a description of Modafinil or adrafinil salts, derivatives and mixtures which are useful in the compositions of the present invention. Nevertheless, Modafinil as the anhydrous powder base is presently preferred and, where specific amounts of Modafinil are set forth below, such amounts are given in mg of the anhydrous powder base.

A number of pharmaceutical compositions containing Modafinil together with a pharmaceutically acceptable carrier have been described in the prior art. See, for example, U.S. Pat. No. 5,618,845 titled "Acetamide Derivative Having Defined Particle Size," granted to Grebow, et al. However, nowhere in the prior art is described nasal administration of Modafinil. It has been discovered that Modafinil-containing compositions can usefully be administered to mammals in nasal compositions at low dosage levels to elicit a systemic therapeutic response and to provide enhanced bioavailability, minimize variations in blood levels, provide more rapid onset of activity, ease of administration, and reduced side effects compared to current oral or parenteral methods of administration. The nasal administration of Modafinil in accordance with the present invention is significantly more efficient than oral or parenteral administration. Simple, small containers such as eye droppers, spray bottles, aerosol or other pressurized containers, and tubes which can be easily carried in a pocket or purse can be used for delivery. Modafinil could be used as a stimulant to prevent sleep, particularly by auto and truck drivers, pilots, etc. Rapid onset of activity and enhanced alertness is obviously important for such use. Self-administration by the nasal route when the driver or operator notices onset of drowsiness, producing rapid onset of enhancement of alertness, is significantly more efficient than oral or parenteral administration. The nasal administration of Modafinil in accordance with the present invention is significantly more efficient at allowing dosage titration through choosing the number of nasal sniffs of Modafinil to produce the desired state and degree of alertness, without the excessive dosing or underdosing which oral or parenteral route can produce.

The present invention provides Modafinil-containing compositions, including gels, sprays and solutions which may be administered in the form of dry powders or drops, all of which are specifically formulated for nasal administration, to permit therapeutic delivery of effective amounts of Modafinil through the nasal mucous membrane. Dry powders and suspensions are applied directly to the nasal cavity by conventional means, for example with a dry powder inhaler, dropper, pipette or spray. The formulations may be provided for administration in single or multidose form. In the latter case a means of dose metering is provided. In the case of a dropper or pipette this may be achieved by the patient administering an appropriate, predetermined volume of the suspension. In the case of a spray, this may be achieved, for example, by means of a metering atomizing spray pump. Intranasal administration may also be achieved by means of an aerosol formulation in which the compound is provided in a pressurized pack with a suitable propellant such as a chlorofluorocarbon (CFC), for example, dichlorodifluoromethane, trichlorofluoromethane or dichlorotetrafluoroethane, a hydrofluorocarbon (HFC), for example, 1,1,1,2-tetrafluoroethane or 1,1,1,2,3,3,3-heptafluoropropane, carbon dioxide or other suitable gas. The aerosol may conveniently also contain a surfactant such as lecithin. The dose of drug may be controlled by provision of a metered valve.

Suspensions containing Modafinil according to the invention may be prepared from solutions or suspensions of Modafinil or suitable physiologically acceptable salts or solvates thereof, by addition of an appropriate amount of a base, such as an inorganic base, preferably an alkali metal hydroxide, most preferably sodium hydroxide. More specifically, the compositions containing Modafinil in accordance with the present invention are for nasal administration and contain a therapeutically effective amount of Modafinil. They are conveniently provided as dry powders or as isotonic aqueous suspensions or viscous compositions which may be buffered to a selected pH. The viscous compositions may be in the form of gels, lotions, ointments, creams and the like, and will typically contain a sufficient amount of a thickening agent so that the viscosity is from about 2500 to 6500 cps, although more viscous compositions, even up to 10,000 cps may be employed. The preferred compositions have a viscosity of 2500 to 5000 cps, since above that range they become more difficult to administer. The nasal composition containing Modafinil according to the invention, can be administered as a dry powder, nasal spray, nasal drop, suspension, gel, ointment, cream or dry powder. The administration of a nasal composition containing Modafinil also may take place using a nasal tampon or nasal sponge. Liquid sprays and drops normally are easier to prepare than gels and other viscous compositions. Additionally, they are somewhat more convenient to administer, especially in multi-dose situations. Viscous compositions, on the other hand are much preferred in the practice of this invention, since they can be formulated within the appropriate viscosity range to provide longer contact periods with the nasal mucosa and reduce the amount of Modafinil per dosage unit necessary to achieve the desired result. For satisfactory intranasal administration, an active ingredient must be presented in a defined particle size and form which is readily absorbed through the nasal mucosa but which is unassociated with any adverse effects such as irritancy. Satisfactory intranasal formulations also must be sufficiently stable, chemically and physically, to be consistently dispensed in accurate metered doses, even after prolonged storage under wide temperature fluctuations. Accordingly, the active ingredient must be compatible with the excipients used in the formulation and should not aggregate in a manner which would result in a loss of accurate dose delivery. Suspensions of Modafinil and suitable physiologically acceptable salts and solvates thereof having a pH in the range of 8 to 12 have excellent dispersion properties and are preferred. In contrast, neutral and acidic formulations containing Modafinil generally do not form readily dispersible suspensions and are less preferred for use as suspensions for intranasal administration. However the pH of the compositions may vary from about 4 to 12. The pH is suitably maintained with a physiologically acceptable buffer, suitably an acetate, phosphate, phthalate or borate buffer. Acetate buffers are preferred for convenience and economy.

Since Modafinil is practically insoluble in water and only slightly soluble in lower alcohols, solubility enhancers such as caffeine and/or dextrose may be included. The dosage of Modafinil may vary appreciably with the age and mass of the patient and other factors readily evaluated by the physician or veterinarian in attendance. Therapeutically effective amounts of Modafinil may vary appreciably if other physiologically active agents are present. However, as a generalization, the compositions of the invention in bulk or unit dosage form will typically contain Modafinil in a concentration of from about 25 to 2000 mg/ml. Typically, the volume of a dosage unit is from about 0.05 to 0.3 ml. According to the current edition of the *Physician's Desk Reference*, "the dose of PROVIGIL [(a brand name for an oral formulation of Modafinil)] is 200 mg/day given as a single dose in the morning." The intranasal administration of Modafinil in accordance with the present invention permits rapid and repeatable achievement of a bioavailability of Modafinil that is in accordance with accepted therapeutic levels.

The desired isotonicity of the Modafinil-containing composition may be accomplished using sodium chloride, or other pharmaceutically acceptable agent such as dextrose, boric acid, sodium tartrate, propylene glycol or other inorganic or organic solute. Sodium chloride is preferred particularly for buffers containing sodium ions. Viscosity of the compositions may be maintained at the selected level using a therapeutically acceptable thickening agent. Methyl cellulose is preferred because it is readily and economically available and is easy to work with. Other suitable thickening agents include, for example, xanthan gum, carboxymethyl cellulose, hydroxypropyl cellulose, carbomer, acacia, bentonite, carboxymethylcellulose sodium, gelatin, guar gum, hydroxyethylcellulose, hydroxypropylmethylcellulose, methylcellulose, tragacanth, and the like. The preferred concentration of the thickener will depend upon the agent selected to achieve the selected viscosity. Viscous compositions are normally prepared from solutions by the addition of such thickening agents. Preferably, suspensions made according to the invention will be thixotropic. Thixotropic suspensions can be obtained by the use of a suitable viscosity enhancer, e.g., Avicel RC 591. In a particularly preferred aspect the invention provides a suspension of Modafinil or a suitable physiologically acceptable salt or solvate thereof and microcrystalline cellulose with sodium carboxymethylcellulose adapted for intranasal administration wherein the pH is in the range of 7 to 12.

Preferred compositions within the scope of this invention also may contain a humectant to inhibit drying of the mucous membrane and to prevent irritation. Any of a variety of therapeutically acceptable humectants can be employed including, for example sorbitol, propylene glycol, or glycerol. As with the thickeners, the concentration will vary with the selected agent, although the presence of or absence of these agents, or their concentration, is not an essential feature of the invention. Enhanced absorption across the nasal membrane can be accomplished employing a therapeutically acceptable surfactant. Typically useful surfactants for these therapeutic compositions include polyoxyethylene derivatives of fatty acid partial esters of sorbitol anhydrides such as Tween 80, Polyoxyl 40 Stearate, Polyoxyethylene 50 Stearate and Octoxynol. The usual concentration of such surfactants typically is from 1% to 10% based on the total weight. Such suspensions may additionally contain other excipients, for example preservatives (such as benzalkonium chloride and phenylethylalcohol), wetting agents/surfactants such as polysorbates (e.g., Tween 80) and sorbitan esters (e.g., Span 80), buffering agents, isotonicity-adjusting agents (e.g., sodium chloride), suspending agents, absorption enhancers, flavoring agents and sweetening agents (e.g., saccharin). Suspensions made according to the invention should be sterile. Sterile formulations may be prepared by methods known in the art, for example, by aseptic manufacture or sterilization of the bulk products. A therapeutically acceptable preservative can be employed to increase the shelf life of the compositions. Benzyl alcohol is suitable, although a variety of preservatives including, for example, Parabens, thimerosal, chlorobutanol, or benzalkonium chloride may also be employed.

A suitable concentration of the preservative will be from 0.02% to 2% based on the total weight, although there may be appreciable variation depending upon the agent selected. The components of the compositions should be selected to be chemically inert with respect to the active agent, i.e., Modafinil. The compositions of this invention may contain one or more other therapeutically active agents together with the Modafinil. These may include, for example, wakefulness-promoting agents or stimulant agents such as methylphenidate, ephedrine, amphetamine, and dextroamphetamine or other therapeutic agents normally employed in conjunction with Modafinil. The nasal pharmaceutical composition in accordance with the present invention alternatively may contain Modafinil and a cyclodextrin and/or other saccharides and/or sugar alcohols. Such compositions result in a potentially increased bioavailability of Modafinil with intranasal administration. The therapeutically effective compositions of this invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent.

Typical compositions of this invention contain the following components per 100 ml:

| | | |
|---|---|---|
| 1. | Benzyl alcohol, NF | 1.50 ml |
| 2. | Sodium chloride, NSP | q.s. |
| 3. | Methyl cellulose, USP (400 cps) | 2.00 gm |
| 4. | Acetic acid, NF | q.s. |
| 5. | Sodium acetate (anhydrous, USP) | q.s. |
| 6. | Sorbitol soln., USP | 5.00 ml |
| 7. | Modafinil | 0.1-40 gm |
| 8. | Water, purified q.s. | 100 ml | pH and tonicity will be adjusted q.s. to assure maximum adsorption and minimal local irritation. They will depend on such factors as concentration of the Modafinil and the form in which it is employed, for example: free base, salt, hydrate, and the like.

The following examples are offered by way of illustration, and not by limitation.

EXAMPLE 1

A 20 mg dose quantity of Modafinil suspended in water and charged to an amber glass ampule containing as follows:

| | |
|---|---|
| Modafinil, USP | 20.0 mg |
| caffeine, anhydrous, USP | 10.0 mg |
| dextrose, anhydrous, USP | 50.0 mg |
| carbon dioxide (propellant) | q.s. |
| water for injection, USP | q.s. 1.0 mL |
| Water, purified q.s. | 100 ml |

EXAMPLE 2

Example 1 was repeated varying the amount of Modafinil between 1 and 40 mg, the amount of caffeine between 5 and 50 mg, and the amount of dextrose between 25 and 75 mg.

The administration of Modafinil through nasal delivery provides several advantages. For one, the administration of Modafinil through nasal delivery bypasses absorption from the intestinal track. Thus, Modafinil-containing compositions can be usefully administered to mammals at low dosage levels to elicit a systemic therapeutic response and to provide enhanced bioavailability, minimize variations in blood levels, and achieve more rapid onset of activity, ease of administration, and reduced side effects compared to most current methods of administration.

Also, the administration of Modafinil through nasal delivery produces desirably high blood levels in a desirably short period of time. Injectable solutions and suspensions of Modafinil can rapidly produce rapid high blood levels, but such compositions require a needle puncture of the recipients skin and tissues which can be painful and must normally be administered under the supervision of trained medical personnel in a doctor's office or out-patient department or hospital. In addition, many people object to injections.

The administration of Modafinil given through nasal delivery results in an increase in the amount of desired active product being absorbed because it is not subject to the higher levels of metabolism or excretion as Modafinil administered in an oral formation.

Moreover, the administration of Modafinil given through nasal delivery is not subject to the same high levels of delay of absorption if given in conjunction with food or other physiologically active agents that slow down the rate of absorption within the gastrointestinal system.

Various changes may be made without departing from the spirit and scope of the invention. For example, the amount of Modafinil administered per dose may be widely varied. Preferably each dose will contain from about 1 mg to about 40 mg. Where caffeine is included, caffeine should be present in the amount of about 5 to 50 mg per dose.

While the invention has been described in considerable detail, the invention disclosed herein is not limited to the actual description, but may be varied. Certain changes and modifications may be made without departing from the spirit and scope of the appended claims.

We claim:

1. A method for promoting wakefulness comprising administering to a mammal by nasal delivery a therapeutically effective amount of Modafinil, wherein said Modafinil comprises particles in the 5 to 10 micron range, together with a humectant to inhibit drying of mucous membranes of the mammal.

2. The method according to claim 1, wherein said Modafinil is administered nasally as an aqueous suspension having a pH in the range of 7 to 12.

3. The method according to claim 1, wherein said Modafinil is administered as nasal drops.

4. The method according to claim 1, wherein said Modafinil is administered as a nasal spray.

5. The method according to claim 1, wherein said Modafinil is administered in a unit dose.

6. The method according to claim 5, wherein said unit does comprises 1 to 40 mg of Modafinil.

7. The method according to claim 5, wherein said unit dose comprises 10-30 mg of Modafinil.

8. The method according to claim 5, wherein said unit dose comprises about 20 mg of Modafinil.

9. The method according to claim 1, wherein said Modafinil is administered as an isotonic aqueous suspension.

10. The method according to claim 1, wherein said Modafinil is administered as a gel, lotion, ointment, or cream.

11. The method according to claim 1, wherein said Modafinil is administered as an aerosol.

12. The method according to claim 2, wherein said Modafinil is administered as an aqueous suspension having a pH in the range of 8 to 12.

13. The method according to claim 1, wherein said Modafinil is administered in combination with a solubility enhancer.

14. The method according to claim 13, wherein said solubility enhancer comprises caffeine or dextrose.

15. The method according to claim 1, wherein said Modafinil is administered in combination with a surfactant or wetting agent.

16. The method according to claim 1, wherein the humectant is selected from the group consisting of sorbitol, propylene glycol, and glycerol.

17. The method according to claim 1, wherein the Modafinil is administered together with a stimulant.

18. The method according to claim 17, wherein the stimulant is selected from the group consisting of methylphenidate, ephedrine, amphetamine, and dextroamphetamine.

19. The method according to claim 1, wherein each dose of Modafinil is administered in combination with 5 to 50 mg of caffeine.

* * * * *